United States Patent [19]

Kritzer

[11] 4,226,233

[45] * Oct. 7, 1980

[54] RESPIRATORS

[75] Inventor: Richard W. Kritzer, Chicago, Ill.

[73] Assignee: Longevity Products, Inc., Chicago, Ill.

[*] Notice: The portion of the term of this patent subsequent to Oct. 18, 1994, has been disclaimed.

[21] Appl. No.: 949,402

[22] Filed: Oct. 10, 1978

[51] Int. Cl.³ .............................................. A61M 16/00
[52] U.S. Cl. ........................... 128/205.13; 128/204.18; 128/207.16
[58] Field of Search ............ 128/208, 206, 205, 145.7, 128/145.8, 203, 266, 173 R, 205.13, 207.14, 207.16; 46/80 R, 180, 181

[56] References Cited

U.S. PATENT DOCUMENTS

| 1,646,530 | 10/1927 | Ferretti | 46/180 |
| 3,155,573 | 11/1964 | Fowler | 128/266 X |
| 3,262,446 | 7/1966 | Stoner | 128/145.7 |
| 4,013,075 | 3/1977 | Cocozza | 128/208 X |
| 4,054,134 | 10/1977 | Kritzer | 128/208 |
| 4,062,358 | 12/1977 | Kritzer | 128/208 |

Primary Examiner—Henry J. Recla
Attorney, Agent, or Firm—Emrich, Root, Lee, Brown & Hill

[57] ABSTRACT

A respirator through which a person may breath air or a mixture of air and oxygen, and which vibrates the material passing through the respirator during inhalation and exhalation in such a manner as to vibrate the cilia in the lungs of the person breathing through the respirator. The respirator also embodying a manually operable member for selectively applying positive pressure to the lungs of the person using the same.

10 Claims, 3 Drawing Figures

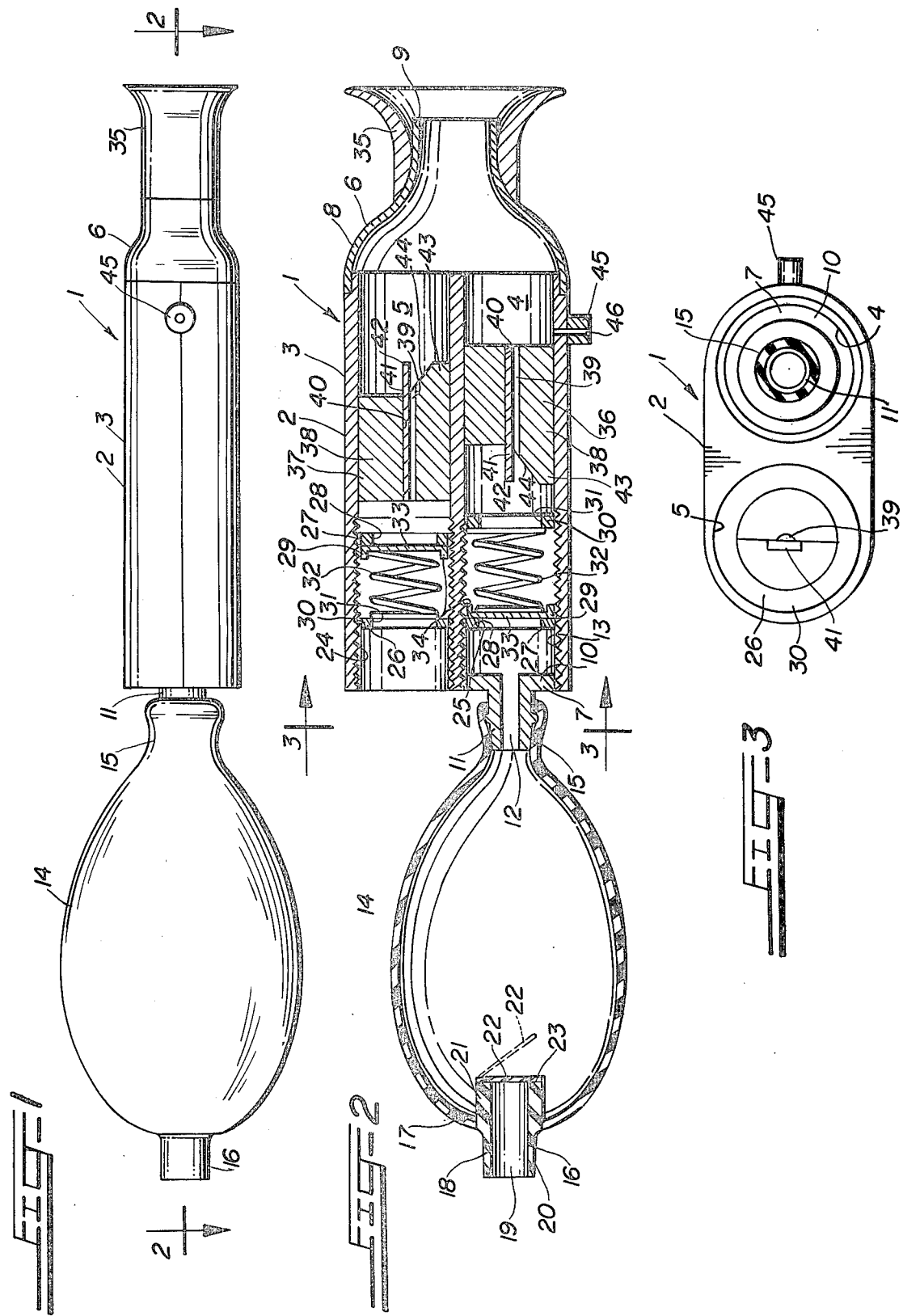

RESPIRATORS

BACKGROUND OF THE INVENTION

This invention relates to respirators, and, more particularly, to respirators that are particularly well adapted for use by persons suffering from emphysema, and the like.

It is a primary object of the present invention to afford a novel respirator.

Another object of the present invention is to afford a novel respirator which is effective to vibrate the material passing therethrough in such a manner that it is effective to vibrate the cilia in the lungs of the person breathing through the respirator.

A further object is to afford a novel respirator which is effective to so vibrate the material passing therethrough both on inhalation and exhalation.

Respirators, which are effective to vibrate material passing therethrough during both inhalation and exhalation, have been heretofore known in the art, being disclosed, for example, in my earlier U.S. Pat. Nos. 4,054,134 and 4,062,358. Respirators of the type disclosed in my aforementioned patents have proven to be very effective. However, it is an object of the present invention to afford improvements over respirators of the type disclosed in the aforementioned patents.

Many persons suffer from ailments, such as, for example, emphysema, or the like, wherein the cilia in the lungs have been flattened down or clogged with mucus, or the like. It is my opinion, which seems to have been borne out by experimentation, that vibration of the air passing into and out of the lungs of a person suffering from the aforementioned conditions is effective to cause cilia, which have been flattened down, to be vibrated into an upstanding position, and to cause cilia which have been clogged with mucus, to be at least partially unclogged. When oxygen being breathed by such a person is vibrated in accordance with my present invention, and in accordance with the teachings of my earlier aforementioned patents, better utilization of the oxygen seems to be effected than when it is not so vibrated.

When respirators of the type disclosed in my aforementioned patents are being used, inhalation therethrough is accomplished by the person using the respirator opening his lungs and allowing the material being inhaled (such as, for example, air or a mixture of air and oxygen) to fill the same. Also, that is true with respect to the initial inhalation, when using a respirator of the type disclosed herein. However, it is my opinion, which seems to be borne out by experimentation, that when, after the aforementioned initial inhalation, when positive pressure is applied to the material being inhaled, the lungs are further open or expanded with the result that the material being vibrated reaches into areas of the lungs not otherwise reached. It is an important object of the present invention to afford a novel respirator by which positive pressure may be applied, in a novel and expeditious manner, to material being inhaled into the lungs of a person using the respirator.

Another object of the present invention is to afford a novel respirator of the aforementioned type wherein the positive pressure applied to the lungs of the person using the same may be readily and effectively controlled by that person.

Machines or attachments, such as, for example, machines or attachments sold by Puritan-Bennett Corporation for use in hospitals, and the like, and which attachments are to be secured to a hospital wall or to an oxygen bottle, or the like, and are effective to apply positive pressure to the lungs of a patient being treated therewith, have been heretofore known in the art. Machines or attachments of the aforementioned type have proven to be effective. However, it is an object of the present invention to afford improvements over such machines or attachments.

Another object of the present invention is to afford a novel respirator of the aforementioned positive pressure type which is readily portable.

An object ancillary thereto is to afford a novel respirator of the aforementioned type which is self-contained.

A further object of the present invention is to afford a novel respirator of the aforementioned positive pressure type which may be readily held in the hand of the person using the same.

A further object of the present invention is to afford a novel respirator of the aforementioned type, which is practical and efficient in operation and which may be readily and economically produced commercially.

Other and further objects of the present invention will be apparent from the following description and claims and are illustrated in the accompanying drawings which, by way of illustration, show the preferred embodiment of the present invention and the principles thereof and what I now consider to be the best mode in which I have contemplated applying these principles. Other embodiments of the invention embodying the same or equivalent principles may be used and structural changes may be made as desired by those skilled in the art without departing from the present invention and the purview of the appended claims.

DESCRIPTION OF THE DRAWINGS

In the drawings:

FIG. 1 is a side elevational view of a respirator embodying the principles of the present invention;

FIG. 2 is a longitudinal sectional view taken substantially along the line 2—2 in FIG. 1; and FIG. 3 is a sectional view taken substantially along the line 3—3 in FIG. 2.

DESCRIPTION OF THE EMBODIMENT SHOWN HEREIN

A respirator or breathing unit 1 is shown in the drawings to illustrate the presently preferred embodiment of the present invention.

The respirator 1 embodies an elongated, tubular housing 2, which is substantially elliptical in transverse cross section, FIG. 3. The housing 2 embodies an elongated tubular body portion 3, having two elongated passageways 4 and 5, which preferably are round in transverse cross-section, extending longitudinally therethrough in side-by-side parallel relation to each other, FIG. 2; an end portion or end cap 6 mounted on one end of the body portion 3; and a supporting member 7 mounted in the end portion of the passageway 4 remote from the end cap 6.

The end cap 6 embodies an inner end portion 8, mounted on one end of the body portion 3 in surrounding relation thereto, FIG. 2, and an outer end portion 9, which is smaller in cross sectional size than the inner end portion 8, and affords a mouthpiece which may be inserted into the mouth of a person breathing through the respirator 1. Preferably, the mouthpiece 9 is substantially elliptical in transverse shape so as to lend itself to ready sealing engagement with the lips of the person in whose mouth it is disposed.

The supporting member 7 embodies a substantially flat body portion 10, which is round in transverse cross section, and a connecting member in the form of a nipple 11, which projects outwardly from the axial central portion of the body portion 10, FIG. 2. A passageway 12 extends axially through the nipple 11 and the body portion 10 of the supporting member 7.

The interior of the passageway 4 in the body portion 3 of the housing 2 has internal threads 13 formed therein. The outer periphery of the body portion 10 of the supporting member 7 is threaded, and in the assembled respirator 1, the supporting member 7 is threadedly engaged with and held by the internal threads 13 in the passageway 4. Preferably, the supporting member 7 is disposed in the extreme outer end of the passageway 4 remote from the mouthpiece 9, as shown in FIG. 2.

An elongated squeeze-bulb 14, made from suitable flexible, resilient material, such as, for example, rubber, has one end portion 15 operatively mounted on the nipple 11 of the supporting member 7, and embodies a one-way valve 16 in the other end portion 17 thereof. The valve 16 embodies an elongated body portion 18, preferably formed integrally with the end portion 17 of the squeeze-bulb 14, having an elongated passageway 19 extending axially therethrough. The body portion 18 has an end portion 20 projecting outwardly from the end portion 17 of the squeeze-bulb 14, for a purpose which will be discussed in greater detail presently, and an inner end portion 21, which projects into the interior of the squeeze-bulb 14, FIG. 2. The valve 16 includes a flapper valve 22, which is mounted on the inner end portion 21 of the body portion 18 and is movable between a closed position, such as shown in solid lines in FIG. 2, wherein it is disposed in abutting engagement with the inner end 23 of the end portion 21 in position to effectively close the passageway 19, and an open position, as shown in broken lines in FIG. 2, to uncover the inner end of the passageway 19. The flapper valve 22 may be made of any suitable material, such as, for example, flexible rubber and may be secured to the body portion 18 of the valve 16 in any suitable manner, such as, for example, adhesively securing a marginal portion thereof to one side of the end 23 thereof.

The passageway 5 in the body portion 3 of the housing 2 also has internal threads 24 formed therein, and the respirator 1 embodies two one-way valves 25 and 26, which are mounted in the threaded portions of the passageways 4 and 5, respectively, in inwardly spaced relation to the supporting member 7 and the end of the passageway 5 remote from the mouthpiece 9, respectively. Each of the valves 25 and 26 is identical in construction, and each embodies an annular seat 27 having a central opening 28 extending therethrough; a valve member 29 movable into and out of engagement with the respective seat 27; an annular retainer ring 30, having a central opening 31 extending therethrough; and a compression coil spring 32 disposed between the valve member 29 and the retainer ring 30 in position to yieldingly normally hold the valve member 29 in engagement with the seat 27. The outer peripheries of the seats 27 and the retainers 30 are threaded, and in the assembled respirator 1, the seats 27 and the retainers 30 of the valves 25 and 26 are threadedly engaged with, and held by the internal threads 13 and 24 in the passageways 4 and 5, respectively.

Each of the valve members 29 has a round, substantially flat body portion 33, from one side of the outer periphery of which projects an annular flange 34, FIG. 2. The valve members 29 are of such size that, when the faces of the body portions 33 thereof remote from the flanges 34 are disposed in abutting engagement with the respective seats 27, the valve members 29 are effective to close the openings 28 through the latter.

In the assembled valves 25 and 26, the retainers 30 and the seats 27 are disposed in spaced relation to each other, with the valve members 29 disposed therebetween in position wherein the flanges 34 project toward the retainers 30, FIG. 2. The springs 32 are disposed between, and are abuttingly engaged with the retainers 30 and the valve members 29 of the respective valves 25 and 26, and are of such size that they fit into the concavity defined by the flanges 34 on the respective valves 29.

The valve members 25 and 26, which it will be remembered are identical in construction, are disposed in reverse relation to each other in the passageways 4 and 5, respectively. Thus, the valve member 25 is disposed in the passageway 4 in position wherein the outer face of the seat 27 thereof faces toward the end of the housing 2 remote from the mouthpiece 9; and the valve member 26 is disposed in the passageway 5 in such position that the outer face of the seat 27 thereof faces toward the mouthpiece 9. Thus, when a person is breathing through the mouthpiece 9, he may exhale through the passageway 5 and inhale through the passageway 4, the valves 25 and 26 being effective to prevent exhalation through the passageway 4 and inhalation through the passageway 5.

With the seats 27 and the retainers 30 of the valves 25 and 26 threadedly mounted in the respective passageways 4 and 5, the seats 27 and the retainers 30 of the respective valves 25 and 26 may be readily adjusted toward and away from each other by rotating the same, to thereby adjust the force with which the respective springs 32 urge the valve members 29 engaged thereby against the adjacent seats 27. Such adjustment is effective to regulate the force with which a person must inhale and exhale through the respirator 1 in order to open the valves 25 and 26, respectively, and thereby cause air to flow through the passageways 4 and 5, respectively, during such inhalation and exhalation. During such inhalation, material, such as, for example, the aforementioned air or a mixture of air and oxygen may pass inwardly through the passageway 19 of the valve 16 into the squeeze-bulb 14, from which it may flow through the passageway 12 in the supporting member 7 into the passageway 4 in the housing 2 to the mouthpiece 9.

In the preferred form of the invention shown in the drawings, a face piece 35, which is of a type well-known in the respirator art, is mounted on the mouthpiece 9 of the cap 6 in surrounding relation thereto. The face piece 35 may be made of any suitable, soft, pliable material, such as, for example, sponge rubber, and flares outwardly from the cap 6. The face piece 35 is so disposed on the mouthpiece 9 of the cap 6, that when the mouthpiece 9 is disposed in operative position in a person's mouth, the face piece 35 is pressed against the face of the person in sealing engagement therewith so as to assist in insuring against leakage between the respirator 1 and the mouth of the person breathing therethrough.

Two vibrators 36 and 37 are mounted in the passageways 4 and 5, respectively. The vibrators 36 and 37 are identical in construction and each embodies an elongated body portion 38, having an elongated passageway 39, which is substantially semi-circular in transverse cross-section, and an elongated channel 40, which is substantially rectangular in transverse cross-section, extending axially therethrough in side-by-side relation to each other.

Each of the vibrators 36 and 37 embodies an elongated reed 41, which is substantially rectangular in transverse cross-section, mounted in the respective channel 40 therein. The reeds 41 preferably are disposed in the channels 40 with a force fit, and, if desired, may be further secured to the respective body portions 38, in which they are mounted, by suitable means, such as, for example, an adhesive, not shown. Each of the reeds 41 has an end portion 42, which projects outwardly away from one end of the respective body portion 38 in which it is mounted.

Each of the body portions 38 of the respective vibrators 36 and 37 embodies a tongue 43, which projects outwardly beyond the end of the passageway 39 adjacent to the end of the channel 40 from which the respective reed 41 projects. The faces 44 of the tongues 43, which face toward the respective reeds 41, slope outwardly away from the respective adjacent passageways 39 at an acute angle to the longitudinal axis of the latter.

It is to be observed that although the vibrators 36 and 37 are identical in construction, they are mounted in the respective passageways 4 and 5 in reverse direction relative to each other, the vibrator 36 being disposed in the passageway 4 in such position that the end portion 42 of the reed 41 thereof projects toward the end portion of the housing 2 remote from the mouthpiece 9, and the vibrator 37 being mounted in the passageway 5 in such position that the end portion 42 of the reed 41 thereof projects toward the mouthpiece 9.

With the vibrators 36 and 37 constructed in the aforementioned manner and operatively so mounted in the respective passageways 4 and 5, air passing through the vibrators 36 and 37 from the end thereof from which the end portions 42 of the reeds 41 projects, during proper inhalation and exhalation, respectively, through the respirator 1, will cause the reeds 41 to be rapidly vibrated and thus cause vibrations to occur in the air in the respirator 1, and in the air in the trachea and lungs of the person breathing through the respirator. Preferably, the vibrations thus caused to occur in the air, or mixture of air and oxygen, passing through the respirator are at such a frequency as to cause sound, which is audible to the human ear to emanate from the respirator 1. One reason that this is preferred is that it affords a means for monitoring the proper operation of the respirator, not only by the person who is breathing through the respirator 1, but also by another person, such as an attendant or nurse, the person monitoring the same being able to determine whether vibrations are being set up during inhalation and exhalation through the respirator 1 by the presence or absence of sound emanating therefrom. Another reason that I prefer that vibrations emanating from the respirator be of a frequency audible to the human ear is that vibrations in the frequencies audible to the human ear appear to cause vibrations of the air in the lungs of the person breathing through the respirator 1 which are effective in beneficially vibrating the cilia in the lungs of the person using the respirator. This is particularly true in the lower ranges of the frequencies audible to the human ear, and as a result, I prefer that, as is true with respect to the vibrators in the respirators disclosed in my aforementioned U.S. Pat. Nos. 4,054,134 and 4,062,358, the vibrators 36 and 37 be such that the vibrations caused by the inhalation and exhalation of a person using my novel respirator 1 be not substantially less than one-hundred vibrations per second and not substantially more than three-hundred vibrations per second.

The reeds 41 of the vibrators 36 and 37 may be made of any suitable material, but, preferably, are made of a suitable composition material, such as, for example, a composition of hard rubber or a suitable plastic material, such as, for example, polystyrene. Similarly, the body portions 38 of the vibrators 36 and 37 may be made of any suitable material, but, preferably, are made of a suitable, relatively hard wood, such as, for example, mahogany, or the like.

Also, the body portion 3 and the end cap 6 of the housing 2 may be made of any suitable material, such as, for example, a suitable plastic material, such as, for example, polypropylene, polyethylene or polystryene, but, preferably, they are made of a suitable wood, such as, for example, white pine, or the like. In addition, the supporting members 7 may be made of any suitable material, but, preferably, are made from a suitable metal, such as, for example, steel, or the like.

A coupling member 45 having a passageway 46 extending therethrough, FIG. 2, is mounted in and extends through the side wall of the body portion 3 of the housing 2 into the passageway 4, between the vibrator 36 and the cap 6. If desired, auxiliary material, such as, for example, a medicant spray or gas may be fed through the passageway 46 into the passageway 4 while a person is using the respirator, so that the auxiliary material mixes with the main material, such as, for example, the aforementioned air or mixture of air and oxygen passing into the respirator 1 through the end portion of the passageway 4 remote from the mouthpiece 9, and is inhaled with the main material into the lungs of the person using the respirator 1.

In the use of the respirator 1, a person, while holding the respirator in one hand, may insert the mouthpiece 9 into his mouth, with the face piece 35 pressed into engagement with his face, and breath inwardly and outwardly through the respirator 1. When the valve 16 is open to the atmosphere, when the person inhales through the respirator 1, air flows inwardly through the valve 16, the squeeze-bulb 14, the nipple 11, the valve 25 and the vibrator 36 in the passageway 4, to the end cap 6, from which it flows outwardly through the mouthpiece 9 into the person's trachea and lungs. The passage of air through the vibrator 36 causes the end portion 42 of the reed 41 thereof to vibrate, to thereby vibrate the material passing through the respirator 1 and cause vibration of the material flowing into the trachea and lungs of the person using the respirator. Subsequently, when the person exhales through the mouthpiece 9, the valve 25 is closed and the material thus expelled from the lungs of the person passes longitudinally through the vibrator 37 and the valve 36 in the passageway 5 and outwardly through the end of the passageway 5 remote from the mouthpiece 9. This flow of material, in proper exhalation, is effective to cause vibration of the end portion 42 of the reed 41 in the vibrator 37, with consequent vibration of the material being exhaled through the respirator 1, which vibrations are transmitted to the air, and the like, in the trachea and the lungs of the person using the respirator. This operation of the respirator 1 is similar to that of the respirators shown in my aforementioned U.S. Pat. Nos. 4,054,134 and 4,062,358.

However, in addition to this operation of the respirator 1, during inhalation, and after the person using the respirator has filled and opened his lungs as far as possible by such inhalation, he may manually squeeze the squeeze-bulb 14, with his free hand, to thereby force additional air into his lungs. This has the effect of opening the lungs further to thereby permit the vibrating material, such as, for example, the aforementioned air or mixture of air and oxygen, to pass into areas in the lungs not previously reached by the material. During such squeezing of the bulb 14, the valve 16 is closed by the outward positive pressure applied to the valve member 22, to thereby prevent the escape of air from the bulb 14 outwardly through the valve 16. When the bulb 14 is released, the valve 16 again opens to permit air to pass inwardly therethrough and again fill the squeeze-bulb 14.

In the above described operation of the respirator 1, wherein positive pressure is applied, through the squeeze-bulb 14, into the trachea and lungs of the person using the same, this pressure is completely controllable by the person using the respirator, the amount and duration of the squeezing force, manually applied to the squeeze-bulb 14 determining the amount of positive pressure air flow into the lungs of the person. Thus, the amount of such air flow may be personally controlled by the person using the respirator, in accordance with his needs and comfort.

As previously mentioned, if desired, rather than having the valve 16 open to the atmosphere, the end portion 20 of the housing 18 thereof may be connected to a suitable source of other material, such as, for example, a tank of medical oxygen or to a mixture of air and oxygen.

From the foregoing it will be seen that the present invention affords a novel respirator which is effective, in a novel and expeditious manner, to feed either air or a mixture of oxygen and air therethrough.

In addition, it will be seen that the present invention affords a novel respirator which is effective to cause the material passing therethrough to vibrate in such a manner as to vibrate the air in the trachea and lungs of a person breathing through the respirator, during both inhalation and exhalation through the respirator.

Also, it will be seen that the present invention affords a novel respirator of the aforementioned type in which, after a patient has inhaled therethrough, additional air of the like may be fed, in a novel and expeditious manner, through the respirator into the lungs of the person to thereby further open the lungs and pass the material being inhaled into portions of the lungs not reached by the material initially inhaled by the person.

In addition, it will be seen that the present invention affords a novel respirator of the aforementioned type, which is practical and efficient in operation, and which may be readily and economically produced commercially.

Thus, while I have illustrated and described the preferred embodiment of my invention, it is to be understood that this is capable of variation and modification, and I therefore do not wish to be limited to the precise details set forth, but desire to avail myself of such changes and alterations as fall within the purview of the following claims.

I claim:
1. A respirator comprising
   a. an elongated tubular housing having a mouthpiece at one end thereof for insertion into a person's mouth and to enable the person to
      (1) inhale in one direction longitudinally through said housing, and
      (2) exhale longitudinally through said said housing in the direction opposite to said one direction,
   b. means in said housing for vibrating material inhaled and exhaled therethrough, and
   c. means connected to said housing for applying positive pressure to material passing through said housing and mouthpiece into such a person's mouth,
   d. said last mentioned means having
      (1) an inlet passageway thereinto, and
      (2) a separate outlet passageway therefrom.
2. A respirator as defined in claim 1, and in which
   a. said means for applying positive pressure is connected to the end of said housing remote from said mouthpiece.
3. A respirator as defined in claim 1, and in which
   a. said means for applying positive pressure comprises a manually operable squeeze-bulb operatively connected to said housing.
4. A respirator as defined in claim 3, and which includes
   a. valve means mounted in said inlet passageway in in position to
      (1) permit said material to pass through said valve means into and through said bulb, and through said housing and mouthpiece into such a person's mouth, and
      (2) prevent said material to pass outwardly from said bulb through said valve.
5. A respirator comprising
   a. an elongated tubular housing having a mouthpiece at one end thereof for insertion into a person's mouth to thereby enable the person to
      (1) inhale in one direction longitudinally through said housing, and
      (2) exhale longitudinally through said housing in the direction opposite to said one direction,
   b. means in said housing for vibrating material inhaled and exhaled therethrough,
   c. said housing having two passageways extending longitudinally through at least a portion thereof in side-by-side relation to each other.
   d. said means for vibrating material inhaled through said housing comprising means mounted in one of said passageways,
   e. said means for vibrating material exhaled through said housing comprising means mounted in the other of said passageways, and
   f. means connected to said housing for applying positive pressure to material passing through said housing and mouthpiece into such a person's mouth,
   g. said last mentioned means having
      (1) an inlet passageway thereinto, and
      (2) a separate outlet passageway therefrom.
6. A respirator as defined in claim 5, and in which
   a. said means for applying positive pressure is operatively connected to the end of said one passageway remote from said mouthpiece.
7. A respirator as defined in claim 5, and in which
   a. said means for applying positive pressure comprises a squeeze-bulb
      (1) operatively connected to the end of said one passageway remote from said mouthpiece, and

(2) manually operable to apply said pressure to material passing through said housing and mouthpiece into such a person's mouth.

8. A respirator as defined in claim 7, and in which
   a. said squeeze-bulb includes a one-way valve mounted in said inlet passageway in position to
      (1) feed said material through said valve into said bulb, and
      (2) prevent said material from passing from said bulb outwardly through said valve.

9. A respirator comprising
   a. an elongated tubular housing having a mouthpiece at one end thereof for insertion into a person's mouth to thereby enable the person to
      (1) inhale in one direction longitudinally through said housing, and
      (2) exhale longitudinally through said housing in the direction opposite to said one direction,
   b. means in said housing for vibrating material inhaled and exhaled therethrough,
   c. said housing having two passageways extending longitudinally through at least a portion thereof in side-by-side relation to each other,
   d. said means for vibrating material inhaled through said housing comprising means mounted in one of said passageways,
   e. said means for vibrating material exhaled through said housing comprising means mounted in the other of said passageways,
   f. means connected to said housing for applying positive pressure to material passing through said housing and mouthpiece into such a person's mouth,
   g. said means for applying positive pressure comprising a squeeze-bulb
      (1) operatively connected to the end of said one passageway remote from said mouthpiece, and
      (2) manually operable to apply said pressure to material passing through said housing and mouthpiece into such a person's mouth,
   h. said squeeze-bulb including a one-way valve mounted therein in position to
      (1) feed said material through said valve into said bulb, and
      (2) prevent said material from passing from said bulb outwardly through said valve, and
   i. said valve including means for connecting said valve to a source of oxygen for feeding such oxygen through said valve into said bulb.

10. A respirator comprising
   a. an elongated tubular housing having a mouthpiece at one end thereof for insertion into a person's mouth to thereby enable the person to
      (1) inhale in one direction longitudinally through said housing, and
      (2) exhale longitudinally through said housing in the direction opposite to said one direction.
   b. means in said housing for vibrating material inhaled and exhaled therethrough,
   c. said housing having two passageways extending longitudinally through at least a portion thereof in side-by-side relation to each other,
   d. said means for vibrating material inhaled through said housing comprising means mounted in one of said passageways,
   e. said means for vibrating material exhaled through said housing comprising means mounted in the other of said passageways,
   f. each of said passageways having
      (1) an annular valve seat mounted therein for the passage of such material therethrough,
      (2) a valve member mounted therein in position to be moved into and out of closing engagement with said valve seat,
      (3) spring means mounted therein and yieldingly engaged with said valve member for yieldingly holding said valve member in said closing engagement with said valve seat, and
      (4) a retainer member mounted therein and engaged with said spring means on the side thereof remote from said valve member in position to hold said spring means in engagement with said valve member,
   g. said valve seats being threaded into respective ones of said passageways and being adjustable longitudinally thereof,
   h. said retainer members being threaded into respective ones of said passageways and being adjustable longitudinally thereof,
   i. said valve member in said one passageway being disposed in said closing engagement during such exhalation through said housing,
   j. said valve member in said other passageway being disposed in said closing engagement during such inhalation through said housing, and
   k. a manually operable squeeze-bulb having separate inlet and outlet passageways, and having said outlet passageway operatively connected to the end of said one passageway remote from said mouthpiece for applying positive pressure to material passing through said one passageway and mouthpiece into such a person's mouth.

* * * * *